United States Patent [19]

Smith et al.

[11] Patent Number: 5,558,086
[45] Date of Patent: Sep. 24, 1996

[54] METHOD AND APPARATUS FOR THE INTERMITTENT DELIVERY OF OXYGEN THERAPY TO A PERSON

[75] Inventors: Donald M. Smith, Vancouver; Roderick M. Townley, Abbotsford, both of Canada

[73] Assignee: Freedom Air Services, Vancouver, Canada

[21] Appl. No.: 347,237

[22] Filed: Nov. 23, 1994

Related U.S. Application Data

[63] Continuation-in-part of Ser. No. 991,824, Dec. 16, 1992, abandoned.

[51] Int. Cl.⁶ ............................. A61M 16/00; A62B 7/00; A62B 9/00; F16K 31/26
[52] U.S. Cl. ............................. 128/204.26; 128/204.23; 128/205.22; 128/205.24
[58] Field of Search ............................. 128/204.18, 204.21, 128/204.23, 204.26, 204.29, 205.22, 205.24

[56] References Cited

U.S. PATENT DOCUMENTS

| | | |
|---|---|---|
| 4,054,133 | 10/1977 | Myers . |
| 4,381,002 | 4/1983 | Mon . |
| 4,457,303 | 7/1984 | Durkan . |
| 4,535,767 | 8/1985 | Tiep et al. . |
| 4,681,099 | 7/1987 | Sato et al. . |
| 4,705,034 | 11/1987 | Perkins . |
| 4,823,788 | 4/1989 | Smith et al. . |
| 4,832,014 | 5/1989 | Perkins . |
| 4,832,041 | 5/1989 | Wang et al. . |
| 4,873,971 | 10/1989 | Perkins . |
| 4,932,401 | 6/1990 | Perkins . |
| 5,005,570 | 4/1991 | Perkins . |
| 5,074,299 | 12/1991 | Dietz | 128/204.21 |
| 5,238,001 | 8/1993 | Gallant et al. | 128/700 |
| 5,449,912 | 9/1995 | Mayer | 250/343 |

OTHER PUBLICATIONS

"7200 Series" Puritan–Bennett, Overland Park, KS, USA, 66225; Forms AA–763 (Mar. 1989), 991 (Dec. 1987), 985 (Jan. 1987), 1143 (Dec. 1987), 992 (Sep. 1988), 1236 (Oct. 1987), 934 (May 1984), 639 (Jun. 1987), 214 (Aug. 1988).

*Primary Examiner*—Kimberly L. Asher
*Attorney, Agent, or Firm*—Oyen Wiggs Green & Mutala

[57] ABSTRACT

A portable apparatus for supplying dosages of an oxygen-containing gas to the respiratory tract of a person in synchronization with the inhalation phase of the respiratory cycle of said person comprising: (a) a low voltage step control relay with an inlet port for connecting to a source of oxygen-containing gas having a gas proportion regulator; (b) a low voltage microbridge mass gas flow sensor connected to a gas outlet for connection to the respiratory tract of the person said gas flow sensor sensing the duration of oxygen containing gas flow during each inhalation phase of the respiratory cycle of the person and transmitting corresponding information to a microcontroller; (c) a programmed low voltage microcontroller for receiving electrical signals from the gas flow sensor upon detection by the gas flow sensor of the beginning or termination of inhalation by the person; (d) a portable low voltage electrical power supply for operating the low voltage gas flow sensor, the low voltage microcontroller, and the low voltage step control relay; (e) a display panel connected to the microcontroller and the gas flow sensor for displaying programmed data from said microcontroller, and data received from said gas flow sensor; and (f) a keyboard connected to said microcontroller for enabling manual commands to be conveyed to said microcontroller.

19 Claims, 10 Drawing Sheets

5,558,086

METHOD AND APPARATUS FOR THE INTERMITTENT DELIVERY OF OXYGEN THERAPY TO A PERSON

This is a continuation-in-part application of application Ser. No. 07/991,824, filed Dec. 16, 1992, now abandoned.

FIELD OF THE INVENTION

This invention pertains to a novel method and apparatus for the intermittent delivery of prescribed long term medical oxygen therapy to a person according to the ventilatory and oxygen requirements of the person. In one aspect, the invention relates to a novel method and apparatus which is portable and thereby enables a person requiring a ventilator to function like a normal person and perform the daily routine of a person who does not require a ventilator.

BACKGROUND OF THE INVENTION

There are many applications where a person requires supplemental oxygen to assist in effective respiration when breathing. Some examples include mining, fire fighting, diving, working in dangerous atmospheres, and flying in small non-pressurized aircraft. In high altitude environments the oxygen available for respiration in ambient air is depleted and supplemental oxygen is also required.

In many of these situations, oxygen is delivered at a steady flow rate and much of the delivered oxygen is wasted. This is because a person needs oxygen available only during the inspiratory phase of their respiratory cycle. Also, most of the oxygen systems used for such applications are heavy and cumbersome, not very portable, and depending on the system used, the oxygen supply may last for only relatively short periods of time.

Patients suffering from certain advanced stages of chronic obstructive pulmonary disease (COPD) are often treated by the administration of long term supplemental oxygen therapy. Common COPD's include pulmonary emphysema, chronic bronchitis, and severe asthma.

Devices which are commonly used to deliver oxygen to a person meter the oxygen at a fixed flow rate and thereby deliver a constant stream of oxygen. The oxygen is received by the person usually through an oxygen mask placed over the nose and mouth, or by nasal oxygen cannula inserted into the external nares of a person's nostrils. An oxygen catheter may sometimes be used to deliver oxygen for transtracheal oxygen therapy.

When breathing, a person inhales and exhales during each respiratory cycle. The inhalation or inspiratory phase is usually of much shorter duration than the exhalation or expiratory phase. This is termed the "I/E Ratio" and is approximately 1:2. There is also a pause at the end of each expiratory phase just prior to inhaling. When oxygen is administered at a steady flow to a person throughout their entire respiratory cycle, it is totally wasted during the exhalation phase, and during this pause. It is also wasted during the latter portion of the inspiratory phase (approximately 50%–60%) due to deadspace ventilation.

As medical oxygen is an anhydrous gas, water must be added with an attached humidifying device when using steady flow rate systems. This is particularly true for long term oxygen therapy. If oxygen is delivered during the first part of the inspiratory phase, a humidifier, with its potential problems of contamination by infection, is not needed.

Devices have been developed to conserve oxygen by intermittently regulating the oxygen flow in response to the inhalation stage of the respiratory cycle. Typical of such devices are those of Myers, U.S. Pat. No. 4,054,133, and Mon, U.S. Pat. No. 4,381,002. Each of these patents disclose devices which sense inhalation and exhalation pressures in the nasal cavity of a patient and convert those sensed pressure differentials to signals which control the flow of oxygen to a patient. Typically, oxygen flow is started upon the sensing of a negative pressure relative to atmospheric indicating the start of an inspiration period. Oxygen flow is then stopped at a second signal produced by the sensing of a positive pressure relative to atmospheric indicating the start of the expiration period.

Sato et al., in U.S. Pat. No. 4,681,099 disclose a non-portable breath-synchronized concentrated oxygen supplier comprising an air compressor, two absorption cylinders, a reservoir tank, an oxygen concentrator for producing and storing oxygen-enriched gas, a buffer tank having an inlet connected to the oxygen concentrator and an outlet for temporarily storing the oxygen enriched gas obtained from the concentrator.

Sato et al. disclose a thermocouple 28 which is used in the nose connecting cannula of the oxygen supplier and is used to directly sense the inspiration and exhalation of the respiration cycle of the patient. The thermocouple generates an output signal indicative of the inhalation and exhalation stages of the respiration. The thermocouple 28 is electrical current intensive and draws a continuous current from the electrical power supply according to a sinusoidal pattern as illustrated in FIG. 4A (column 10, lines 50 to 57). This continuous current draw necessitates large power requirements. Sato et al. also disclose a breath synchronizing solenoid valve 24 which is controlled by a gas regulator 29. The regulator 29 electrically opens the solenoid valve 24 at the beginning of each inhalation phase and maintains the solenoid valve in an open position for a length of time by delivering a continuous electrical current to the solenoid valve 24. The open time is based on a period determined by a combination of averaging the preceding inhalation durations in the ratio set on an input device. A continuous flow of electrical current is required in order to maintain the solenoid valve 24 in an open position during the majority of each inhalation phase as demonstrated in FIG. 4B. The breath-synchronized concentrated oxygen supplier disclosed by Sato et al. is not suitable for portable use because it continuously consumes substantial amounts of electrical power which quickly drains a battery system. No teaching or suggestion of conserving electrical power consumption is demonstrated in Sato et al.

The Puritan-Bennett 7200 Series respirators are complex, expensive, non-portable systems. The 7200 Series respirators require hook-up to a constant source of electrical current, typically a wall plug or the like. Further, while the Puritan-Bennett 7200 Series Respirators disclose a number of sensors, and sophisticated programming which can be manually manipulated to correspond with breathing cycles of specific patients, including assisting in respiration of a patient, there is no disclosure in the 7200 Series brochures which teaches the applicant's unique concept of prolonging the life of a portable battery, and the oxygen delivering respiratory gas system, by minimizing electricity consumption. This is done by drawing the electrical current in two brief pulses, coordinated respectively with the onset and termination of the inspiration phase of the patient. As explained above, this feature vastly prolongs the life of the applicant's unique apparatus. Since the Puritan-Bennett 7200 Series respirators are connected to permanent sources of power supply, the concepts of portability, and minimizing battery current demand, do not arise.

It is noted that even if the teachings of Sato et al. and Puritan-Bennett 7200 Series are combined, a possibility, incidentally, which is not taught in either citation, one still does not arrive at the applicant's unique portable respiratory system. One still would not devise a portable oxygen supply system which delivered brief pulses of electrical current at the beginning and the end of inspiration of a patient.

Durkan, in U.S. Pat. No. 4,457,303, describes a respirator system which uses a fluidic laminar proportional amplifier to sense the start of an inspiration period. Oxygen flow to a patient is immediately started in response to the sensed inspiration. Timing means, also started in response to the sensed inspiration, stops the oxygen flow after a preset period of time which is shorter than the inspiration period. As a result, oxygen is supplied to a patient only during the effective early stages of an inspiration resulting in an oxygen savings of as much as 70 percent as compared to a continuous flow administration.

Perkins, in U.S. Pat. No. 4,705,034, Nov. 10, 1987, U.S. Pat. No. 4,873,971, Oct. 17, 1989 and U.S. Pat. No. 5,005,570, Apr. 9, 1991, discloses a device for administering oxygen and other respirating gases to a patient which premeters and temporarily stores single does quantities of respirating gas and dispenses each dose in synchronization with the patient's inspiratory cycle. A sensor produces a signal upon the onset of each inhalation and a single dose of gas is dispensed to the patient in immediate response to the sensor signal.

Smith et al., U.S. Pat. No. 4,823,788, Apr. 25, 1989, disclose a method and apparatus for computer controlling the flow of breathing gas such as oxygen through a cannula or "mask" to a person by limiting gas delivery to the inhalation part of the breathing cycle. A bidirectional dynamic mass flow sensor senses the rate of flow of a gas through it and yields an output voltage proportional to mass flow and direction of gas movement. The measured dynamic flow signal is applied to a system computer controller which operates a flow controller. The system computer controller provides for indications of operation such as system failure and apnea, rate of flow, duration of flow, and total consumption. In addition, computer controls are provided to set the duration of gas flow in each breathing cycle.

Perkins, in U.S. Pat. No. 4,932,401, Jun. 12, 1990, discloses a displacement metering device for administering a mixture of oxygen and an anaesthetic gas to a patient, which measures single dose quantities of each of the two gases in separate sets of gas displacing means and dispenses a dose of each gas in admixture to a patient during the inspiration phase of the patient's respiratory cycle. Coordinating means ensure that the two gases are delivered in constant ratio and also provide means for changing the ratio between the two gases. Means are also provided to change the volume or dose size, of the two administered gases.

None of these devices disclose a means for measuring total oxygen consumed by the person so that this quantity can be accurately measured. There is therefore no way that health authorities and social medicine regulatory bodies which operate medical assistance programs, can monitor the amount of oxygen consumed and hence prevent fraudulent claims of oxygen consumption to be policed.

None of these patents disclose an oxygen controller and respiratory monitor which has a liquid crystal display face which on command will display a wide variety of information about the person consuming the oxygen, the condition of the monitor, and other critical parameters.

None of these references demonstrate an oxygen controller and respiratory monitor which by conserving the consumption of electricity, is readily portable and self-sustaining for long periods of time and can be connected to a personal computer-printer.

SUMMARY OF THE INVENTION

The invention is directed to a portable apparatus for carrying by a person and supplying dosages of an oxygen-containing gas to the respiratory tract of the person in synchronization with the inhalation phase of the respiratory cycle of said person, comprising: (a) a low voltage step control relay with a gas inlet port on the apparatus for connecting to a source of oxygen-containing gas; said step control relay being reciprocally moved from a closed non-gas flow position to an open gas flow position by being activated with an electrical signal from a microcontroller of sufficient length of time to open said step control relay; said step control relay after being opened, remaining in an open gas flow position without drawing further electrical current; said step control relay being moved from an open gas flow position to a closed non-gas flow position by being deactivated with a subsequent electrical signal from the microcontroller of sufficient length of time to close said step control relay; (b) a low voltage microbridge mass gas flow sensor connected to a gas outlet port on the apparatus for connection to the respiratory tract of the person, said gas flow sensor sensing the commencement of inhalation, the duration of oxygen containing gas flow, and the termination of inhalation during each inhalation phase of the respiratory cycle of the person and transmitting corresponding commencement, duration and termination information to a microcontroller; (c) a programmed low voltage microcontroller for receiving a first electrical signal from the gas flow sensor upon detection by the gas flow sensor of the commencement of inhalation by the person, and for transmitting a first electric signal to the step control relay of sufficient duration to cause the step control relay to move to an open gas flow position; and for receiving a second electrical signal from the gas flow sensor upon detection by the gas flow sensor of the termination of inhalation by the person, and for transmitting a second electric signal to the step control relay of sufficient duration to cause the step control relay to move to a closed non-gas flow position; (d) a portable low voltage electrical power supply for operating the low voltage step control relay, the low voltage gas flow sensor and the low voltage microcontroller; (e) a display on the apparatus connected to the microcontroller and the gas flow sensor for displaying programmed data from the microcontroller, and data received from the gas flow sensor; and (f) a keyboard on the apparatus connected to the microcontroller for enabling manual control commands to be conveyed to the microcontroller.

The step control relay of the apparatus can comprise an on-off reciprocating valve incorporating a step controlled latching solenoid. The gas flow sensor can be constructed of dual sensing elements flanking a central heating element, and by means of an unsupported thin film with low heat capacity, can sense the commencement and the termination of gas flow inhalation by the person.

The step control relay can have an oxygen inlet port and an air inlet port, and can be equipped with a regulator that blends the oxygen and the air according to a ratio determined by the microcontroller. The microcontroller can be electronically supported by a crystal which acts as a time base and time regulates the microcontroller. The display can be a low voltage liquid crystal display.

The apparatus can include random access memory means connected to the microcontroller and the liquid crystal display. The microcontroller can be connected to a piezobuzzer on the apparatus, the microcontroller activating the piezobuzzer when a predetermined condition programmed into the microcontroller occurs.

The apparatus can include a data output port on the apparatus which is connected to the microcontroller and enables the apparatus to be connected to an exterior microprocessor. The apparatus can include an oximeter sensor connected from the person to the microcontroller for monitoring the pulse rate of the person.

The keyboard can include a manual control to enable a person to call up assorted programmed messages or data on the liquid crystal display. It can also include a manual control which enables said microcontroller to operate in a programmed automatic mode.

The step control relay, the gas flow sensor, the microcontroller and the electrical power supply can be housed in a protective case, the display panel and keyboard can be mounted on the exterior of the case, and the gas inlet port and the gas outlet port can be mounted in the exterior walls of the case.

A cannula or mask can be connected to the gas outlet port for discharging gas into the nasal passages of the person, wherein the person, through the cannula or mask, transmits gas pressure changes to the gas flow sensor, which responds to gas pressure changes indicative of the commencement or termination of inhalation by the person, and transmits corresponding electrical signals to the microcontroller.

The portable power supply can be a rechargeable long-life battery and the battery can be a rechargeable lithium battery.

The apparatus can include a light emitting diode on the apparatus which illuminates when the electrical current level of the battery drops below a predetermined level.

The invention is also directed to an apparatus for carrying by a person and supplying dosages of an oxygen-containing gas to the respiratory tract of the person in synchronization with the inhalation phase of the respiratory cycle of the person comprising: (a) a low voltage step control relay with an on-off reciprocating valve with a step-controlled latching solenoid, and a gas inlet port on the surface of the apparatus for connecting to a source of oxygen-containing gas having a gas proportion regulator; the step control relay being reciprocally moved from a closed non-gas flow position to an open gas flow position by being activated with an electrical signal from a microcontroller of sufficient length of time to open the step control relay; the step control relay remaining in an open gas flow position without drawing further electrical current; the step control relay being moved from a gas flow open position to a closed non-gas flow position by being deactivated with a subsequent electrical signal from a microcontroller of sufficient length of time to close the step control relay; (b) a low voltage microbridge mass gas flow sensor constructed of dual sensing elements flanking a central heating element, and by means of unsupported thin film with low heat capacity, senses gas flow, the gas flow sensor being connected to a gas outlet port on the surface of the apparatus for connection to the respiratory tract of the person, the gas flow sensor sensing the commencement of inhalation, the duration of oxygen containing gas flow, and the termination of inhalation, during each inhalation phase of the respiratory cycle of the person and transmitting corresponding commencement, duration and termination information to a microcontroller; (c) a programmed low voltage microcontroller for receiving a first electrical signal from the gas flow sensor upon detection by the gas flow sensor of the commencement of inhalation by the person, and for transmitting a first electric signal to the step control relay of sufficient duration to cause the step control relay to move to an open gas flow position; and for receiving a second electrical signal from the gas flow sensor upon detection by the gas flow sensor of the termination of inhalation by the person, and for transmitting a second electric signal to the step control relay of sufficient duration to cause the step control relay to move to a closed non-gas flow position; (d) a portable low voltage rechargeable lithium battery for supplying electrical power for operating the low voltage gas flow sensor, the low voltage step control relay, and the low voltage microcontroller; (e) a liquid crystal display panel on the surface of the apparatus connected to the microcontroller and the gas flow sensor for displaying programmed data from the microcontroller, and data received from the gas flow sensor; (f) a keyboard on the surface of the apparatus connected to the microcontroller for enabling manual commands to be conveyed to the microcontroller; and (g) a cannula or mask connected to the gas outlet port for discharging gas into nasal passages of the person, wherein the person, through the cannula or mask transmits gas pressure changes to the gas flow sensor, which responds to gas pressure changes indicative of the commencement or termination of inhalation by the person, and transmits corresponding electrical signals to the microcontroller.

The microcontroller can tally the cumulative sum of oxygen consumed by the person over a given length of time.

The invention is also directed to a method for supplying on a portable basis doses of oxygen containing respirating gas to a mobile person in synchronization with the inspiration and expiration phases of the respiratory cycle of the person comprising: (a) sensing with a gas flow sensor carried by the person or accompanying the person, the commencement of an inspiration phase of the respiratory cycle of the person, and delivering a first electronic signal to a portable programmed microcontroller carried by the person, the microcontroller then transmitting a first electronic signal to a step control relay carried by the person, or accompanying the person, which opens a valve to a portable oxygen source carried by ther person, or accompanying the person, according to a dose prescribed by the programmed microcontroller, and delivers the oxygen to the person through a cannula, the step control relay staying in an open position during the duration of the inspiration phase of the person without drawing electrical current; and (b) sensing with the gas flow sensor the termination of the inspiration phase of the respiratory cycle of the person, and delivering a second electronic signal to the portable programmed microcontroller, the microcontroller then transmitting a second electronic signal to the step control relay which then causes the valve to the portable oxygen source to close and terminate the delivery of respiratory gas to the person.

The respiratory gas can be discharged into the nasal passages of the person, and the person can transmit respiratory gas pressure changes to the gas flow sensor, which responds to gas pressure changes indicative of the commencement or termination of inhalation by the person, and transmits corresponding electrical signals to the microcontroller.

BRIEF DESCRIPTION OF THE DRAWINGS

In drawings which illustrate specific embodiments of the invention, but which should not be construed as restricting the spirit or scope of the invention in any way.

DETAILED DESCRIPTION OF SPECIFIC EMBODIMENTS OF THE INVENTION

Figure 1:
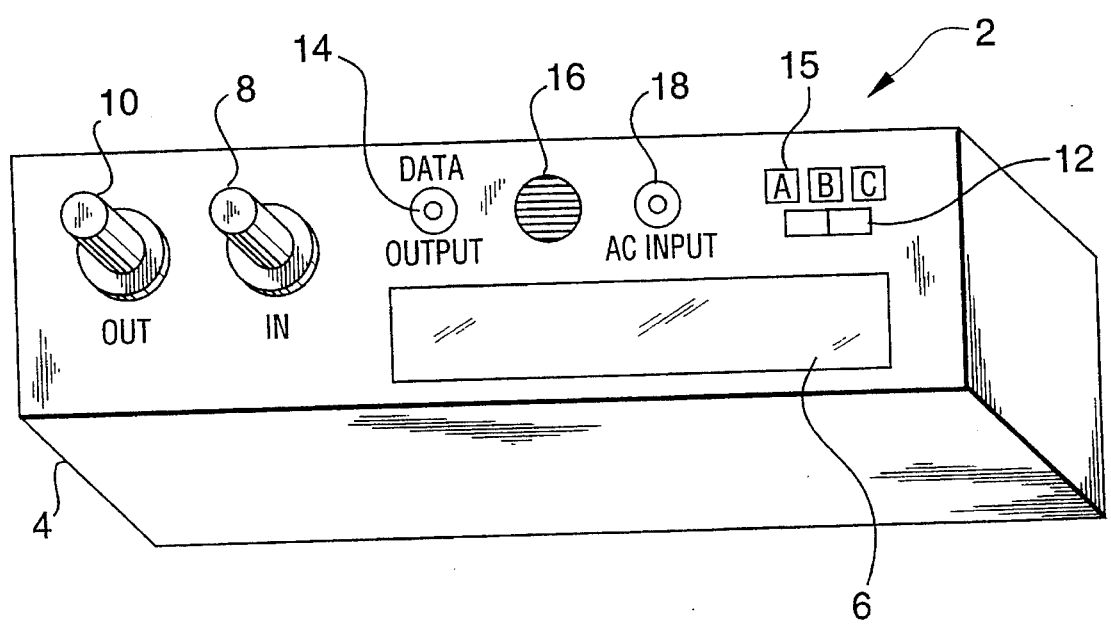
FIG. 1 illustrates a schematic diagram of the demand oxygen controller and respiratory monitor.

The demand oxygen controller and respiratory monitor (DOCARM) of the invention provides a unique high technology readily portable breath sensor which delivers oxygen and respiratory gases only when the user person inspires, and monitors, adjusts, alerts and displays a number of important parameters pertaining to the person such as low battery alarm, apnea alarm, battery charge, total oxygen consumed, oxygen flow rate, time data, average pulse rate and pulse off-time, computer alert and error number. The demand oxygen controller and respiratory monitor automatically adjusts to different atmospheric conditions and elevations. A typical method of oxygen supply to the user is through a mask or nasal cannula. The sensing device used in the demand oxygen controller and respiratory monitor is extremely sensitive and is triggered by a very small vacuum created across the mask or cannula on inspiration. A pressure drop as low as 0.02 mm $H_2O$ is registered even when the user is asleep, that is, breathing with the mouth open, and little air is drawn through the nostrils.

A typical person requiring liquid oxygen has the following equipment in the home. A 40 liter liquid oxygen reservoir constructed of stainless steel. This reservoir permits easy connection to and filling of the DOCARM, which is a flowmeter and intermittent controller according to the invention. This invention (DOCARM) allows pulsed oxygen delivery from the main reservoir to the user while at home, or in the workplace. A 40 liter pulse controlled oxygen tank usually requires filling only once every two or three weeks, and allows refilling of the portable unit. A 1 liter low current battery supplied intermittent controlled portable unit, which can be carried on the back, typically allows up to fourteen hours or more user travel without refilling. The time can be longer by recharging of the battery and depending on oxygen usage.

The invention (DOCARM) senses every breath of the user and delivers a precisely measured dose of oxygen only when the user inhales. As a general rule, the user will inhale a suitable mixture of oxygen and air because sufficient ambient air will seep around the mask or nasal cannula and mix with the oxygen during inhalation by the user. However, as an option, each dose of oxygen can be automatically blended with incoming air so that humidity levels throughout the respiratory system remain within normal limits. The invention (DOCARM) has lighted indicators (LED's) and a liquid crystal display face which show a variety of useful data including oxygen delivery, total oxygen volume consumed over a given time, low battery and charging mode, pulse rate and pulse off-time. The invention (DOCARM) also is equipped with an audible piezo-electric alarm which indicates user apnea or malfunction of the demand oxygen controller and respiratory monitor. In the event of a power outage, the invention (DOCARM) automatically switches to continuous oxygen flow. The invention (DOCARM) also has an output mode which can be connected to a computer-printer. If oxygen use is over a predetermined limit, a piezoelectric alarm sounds. The invention includes a unique on-off step relay which works with the oxygen sensor and uses minimal electrical current from a rechargeable lithium battery to prolong the operative life of the invention without requiring a recharge. The on-off step relay is opened on commencement of inhalation by a first brief electrical signal from the microcontroller, stays open without further electrical current consumption, and is then closed by a second brief electrical signal from the microprocessor on termination of exhalation.

Referring to the drawings, FIG. 1 illustrates an isometric view of the exterior of one version of the demand oxygen controller and respiratory monitor 2, which consists of a protective case 4 which has on the front face thereof a liquid crystal display panel 6, an oxygen inlet 8, an oxygen outlet 10, an on-off switch 12, a data output 14, a keyboard switch 15, and a piezobuzzer alarm 16. The liquid crystal display panel 6 operates on low electrical power, and typically has a 16 character alpha display easy-to-read face. The data output 14 can be connected to and operate a computer-printer and provide a printout report. The data output 14 can also be connected to a conventional telephone jack for relay of data or connected to a pager carried by a nurse or attendant. The overall flow rate of the oxygen from the oxygen source can be controlled by regulating either oxygen input connection 8 or oxygen connection output 10. However, the oxygen rate (and air flow if that option is used) is principally regulated by an on-off step-relay (not shown). The display panel 6 can display any one of a large number of messages or data including low battery alarm, apnea alarm, battery charge, total oxygen consumed, oxygen flow rate, date and time, average pulse rate and average pulse off-time of the user, an alert to reset the computer and an error number. Up and down buttons on the keyboard switch 15 permit the user or an attendant to call up different data on the display panel 6.

Figure 2:
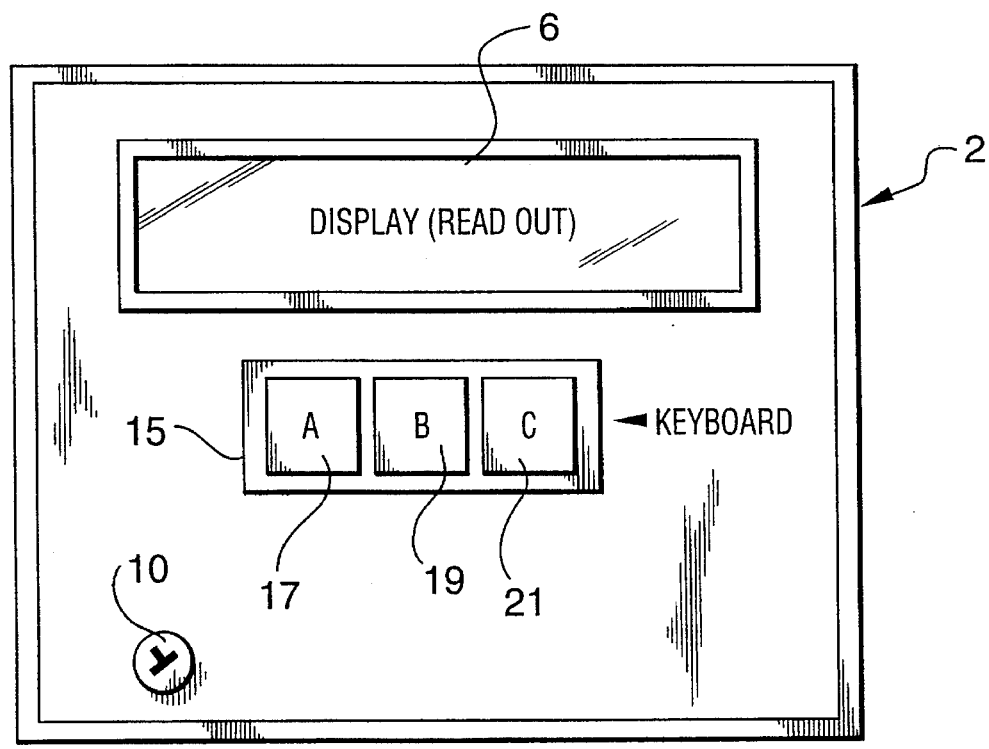
FIG. 2 illustrates a front view of the face of an alternative embodiment of the demand oxygen controller and respiratory monitor.

FIG. 2 illustrates a front view of the face of the demand oxygen control and respiratory monitor 2. The front face includes the liquid crystal display 6, the oxygen outlet 10 and the keyboard 15. The keyboard 15 comprises three buttons or finger pressure locations 17, 19 and 21. The "A" button 17 can be an "up" arrow which, when pressed, causes relevant messages or data in upwardly programmed sequence to appear in series, much like the "up" arrow on a personal computer. The "B" button 19 can be a "down" arrow which operates in reverse to the "A" button 17. The "C" button can be automatic mode, thereby permitting the user to allow the monitor 2 to operate in automatic programmed mode.

The buttons 17, 19 and 21 can be located under a laminated face and activated by finger pressure, similar to control buttons on a microwave oven. The advantages of having the buttons or pressure points under a laminate is that they are then not vulnerable to malfunction from dirt, oil, humidity or water.

Figure 3:
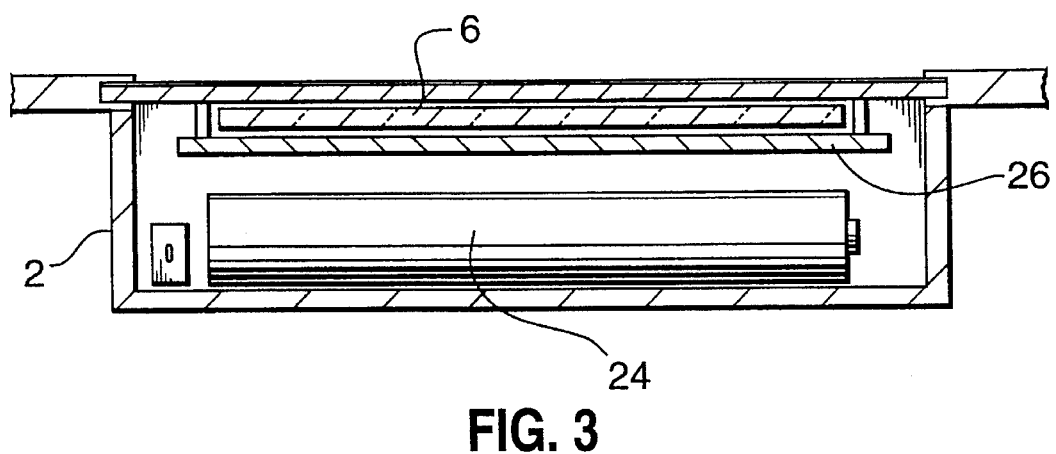
FIG. 3 demonstrates an end section view of the demand oxygen controller and respiratory monitor.

FIG. 3 illustrates an end section view of the monitor 2. The crystal display face 6 is located immediately under the front face. The microprocessor 26 which is in the form of a computer board, or chip, is mounted under the display 6. The rechargeable lithium battery 24 is mounted in the lower part of the housing and can be removed if required.

Figure 4:
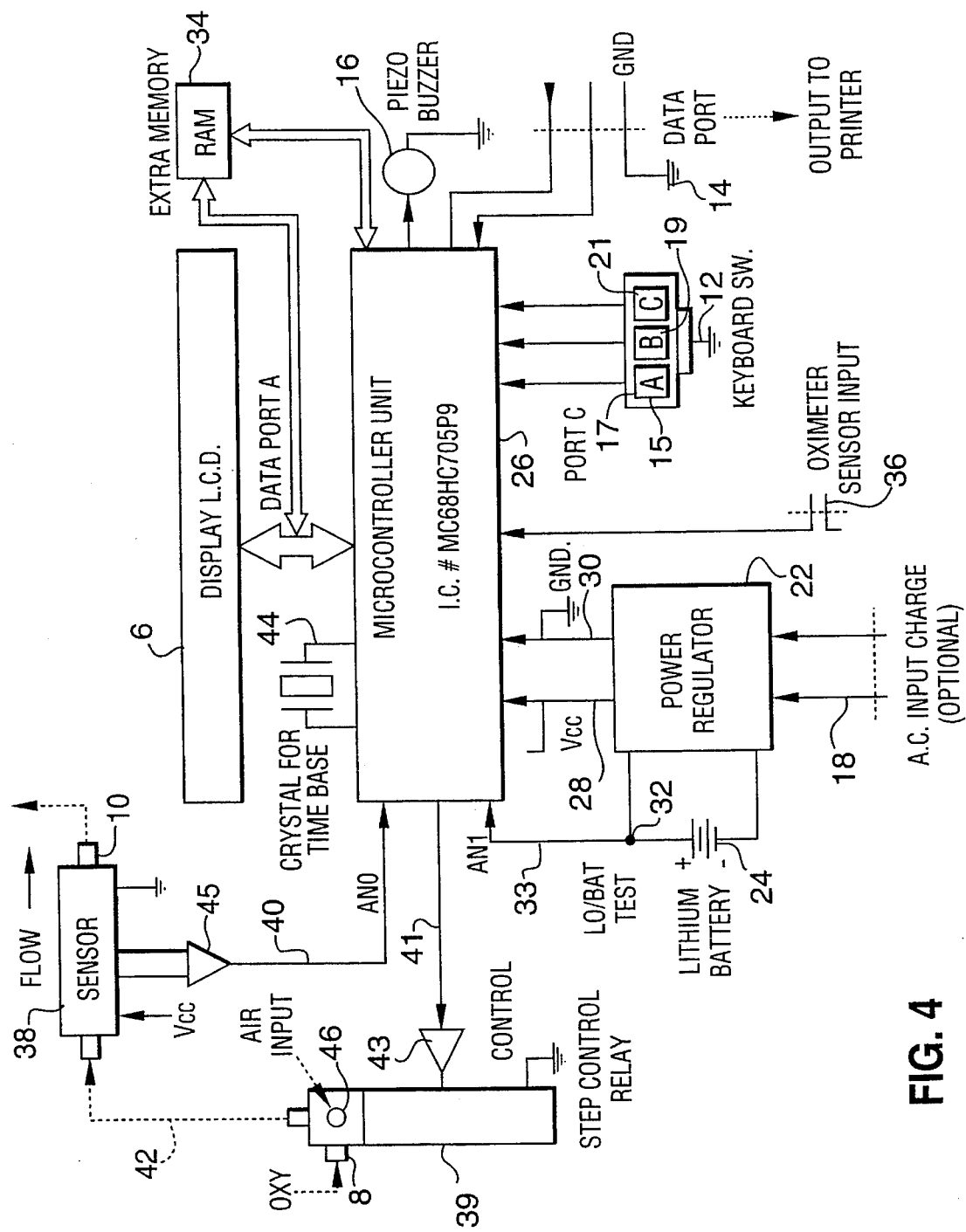
FIG. 4 illustrates a schematic diagram of the electronic components of the demand oxygen controller and respiratory monitor.

Referring to FIG. 4, which illustrates a schematic view of the demand oxygen controller and respiratory monitor 2, the unit can run on an optional power regulator 22, which is supplied by AC input 18, or a rechargeable lithium battery 24. A long life rechargeable lithium battery is preferred and is available from Moli Energy (1990) Ltd., Burnaby, B.C., Canada. The rechargeable battery 24 is extremely useful when the monitor 2 is put in portable mode. This enables the user to operate free of an AC power supply. The user can function normally in a workplace environment and hold down a steady job. The low current rechargeable battery or optional power regulator drives a low current consumption microcontroller unit 26.

A suitable microcontroller unit 26 is available from Motorola, Model No. MC688C705P9. Low voltage current is supplied to the microcontroller unit 26 via a power supply wire 28 and ground wire 30 combination. The microcontroller unit 26 can operate from a single 5-volt power supply, including a rechargeable lithium battery. The microcontroller unit 26 has 2K of read-only memory (ROM program), a serial input/output, and a 4 channel 8-bit A/D converter.

An external power supply can be hooked up to the monitor 2 by AC input wires or connections 18. These connections 18 can also be used to recharge the battery 24. Power from the external AC source is regulated by regulator 22. A low battery test diode 32 is connected between the battery and the microcontroller 26. The diode 32 lights when current flow reaches a predetermined low level. Low battery current data is also transmitted to and processed by the microcontroller 26 via connection 33 and can be displayed on the display 6, either automatically or upon demand by activity button 17 or 19.

Current to the microcontroller unit 26 can be controlled by keyboard switch 12. As explained previously, buttons A (17) and B (19) can be "up" and "down" buttons respectively to bring assorted readings up on the liquid crystal display face 6. Keyboard button C (21) can be a mode button to enable the unit (2) to operate in automatic mode. A standard crystal 44 is connected to the microcontroller unit 26 to act as a time base reference for the unit 26.

The liquid crystal display face 6 is connected to the microcontroller unit 26 as indicated in the schematic diagram. Random access memory (RAM) unit 34 provides extra memory and computer capability to the microcontroller unit 26 as indicated by the conducting arrows. The extra memory is necessary to enable hook-up with an external computer-printer. Data port 14, which is connected to the microcontroller unit 26, enables the monitor 2 to be connected to an outside computer-printer such as a standard personal computer system, available from IBM or the like, to enable readings to be obtained and printout reports to be generated. Piezobuzzer 16 is also driven by the microcontroller unit 26 as indicated in the Schematic diagram. The buzzer 16 is activated when anyone of a number of predetermined conditions occur such as apnea, low battery or malfunction.

The microcontroller unit can optionally receive a signal transmitted by oximeter sensor 36. This oximeter input 36 is typically connected to the person and monitors average pulse rate and average pulse off-time, and respiratory flow of the person. Such sensors are typically conventional fibre optic light sensors that can be connected to the user's nose or finger. These sensors sense and monitor blood flow and transmit the data to the microcontroller 26. A microcontroller unit 26 can be programmed to set off an apnea alarm, if respiratory rate of the person is lower than a predetermined level. Apnea is suspension of breathing of the person.

The microcontroller unit 26, by means of AND gates and signals from the gas flow sensor 38, controls a step control relay 39 which controls oxygen input from an oxygen source such as a tank through oxygen input connection 8.

The step control relay 39 is an on-off solenoid activated valve system which is activated, ie. opened, by a brief "on" electrical signal commanded by the microcontroller 26. Once the step control relay 39 is in an open position, it stays open without consuming further electrical current. The step control relay 39 is moved to a closed position by a second "off" electrical signal commanded by the microcontroller 26. The microcontroller unit 26 controls step control relay 29 via connection 41 and one-way microcontrol 43. As an option, step control relay 39 can have a gas proportion regulator which is capable of automatically blending air from air input 46 with the oxygen received through inlet 8. This ensures consistent humidity and blended oxygen-air proportions according to localized conditions affected by humidity and atmospheric elevation. At higher elevations, more oxygen is required to provide the proper amount of oxygen to the user. The oxygen, which is typically the case, or the blended oxygen-air, if step control relay 39 has a blending option, is delivered to the sensor 38 via delivery line 42. The operation of the step control relay 39 will be discussed later in more detail in association with FIG. 9 and FIG. 17.

Microcontroller unit 26 responds via microcontrol 45 and connection 40 to signals from low voltage oxygen flow sensor 38, which senses and meters the timing and duration of oxygen through oxygen outlet 10 delivered to the user. Sensor 38 includes a micro switch which controls the flow of oxygen or oxygen-air to the user. The flow sensor 38 features a low power stepper valve (not shown) to prolong the life of the lithium battery 24. The flow sensor 38 senses the duration of oxygen or oxygen-air flow during each respiratory cycle, and exhalation back pressure and transmits this data to the microcontroller 26. The flow sensor 38 is compact in size, has low current consumption, and is lightweight, thereby minimizing the overall weight and power requirements of the monitor 2.

A suitable microbridge mass air flow sensor 38 is available from Microswitch, a division of Honeywell as Model No. PK88543. The microbridge mass air flow sensor 38 relies on the extremely low heat capacity of an unsupported thin film as its basis of operation. Dual sensing elements, flanking a central heating element, allow direction of gas flow, as well as rate of gas flow to be sensed. The sensor 38 is comprised of two wheatstone bridges, one for closed loop heater control, and one for the twin sensing elements. The microbridge chip is fundamentally a mass flow sensor using a thermal transfer mechanism. The more mass flowing past the chip, the more heat that is transferred. When sensing a sampled flow of the main flow, the sensing range can be expanded by decreasing the ratio of the main flow diameter to the minimum diameter of the air flow tube within the sensor. By constricting flow, it is possible to measure differential pressure as being proportional to mass flow. Thus, the greater the differential pressure, the more mass that is flowing.

The gas flow data sensed by sensor 38 is processed by the microcontroller unit 26 and enables the microcontroller unit 26 to regulate the operation of the step control relay 39 via connection 41 and microcontrol 43. In this way, the flow of oxygen or oxygen-air through delivery line 42 to sensor 38 is regulated according to the respiration demands of the user as sensed by the sensor 38. The microcontroller 26 signals the draw of a small intermittent amount of low voltage current from the battery 24 through connections 28, 30 or 33, as required by the step control relay 39, when it is activated from an "off" position to a temporary "on" position. This operation will be explained in more detail in association with FIG. 9.

Figure 5:
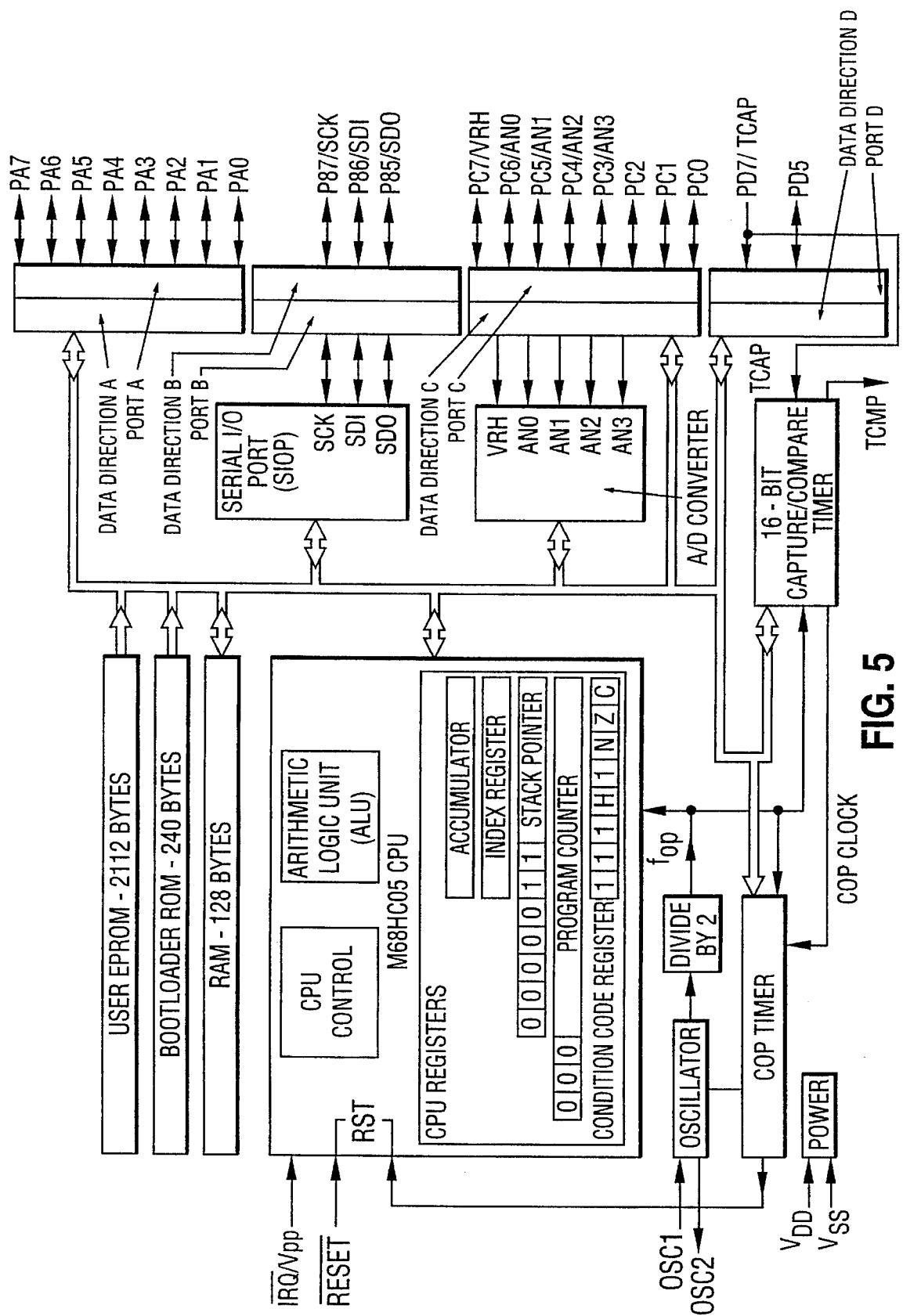
FIG. 5 illustrates a schematic block diagram of the functional components of the microcontroller of the demand oxygen controller and respiratory monitor.

FIG. 5 illustrates a schematic block diagram of the functional components of the microcontroller unit 26. The microcontroller 26, as indicated, has several ports identified as port A, port B, port C and port D. These ports are connected to the buttons 17, 19 and 21 of the keyboard switch 15 and the data output port 14 of the monitor unit 2.

The microcontroller unit 26 is available from Motorola under Model No. MC68HC705P9. It is a high performance (High-Density complementary metal-oxide semiconductor (HCMOS) microcontroller unit (MCU)), low cost system available on a single chip. The MCU features include the following: (1) M68HC05 central processor unit (CPU); (2) Memory-mapped input/output (I/O) registers; (3) 2112 bytes of erasable programmable read-only memory (EPROM) including 16 user vector locations; (4) 128 bytes of static random access memory (SRAM); (5) 20 bidirectional I/O lines and one input-only line; (6) Synchronous serial input/output port (SIOP); (7) Fully static operation (no minimum clock speed); (8) On-chip oscillator with crystal connections; (9) 16-bit capture/compare timer; (10) Four-channel 8-bit A/D converter; (11) Power-saving STOP, WAIT, and data-retention mode; (12) Single 3.3-volt to 5.0-volt power requirement; (13) Selectable computer operating properly (COP) timer.

Figure 6:
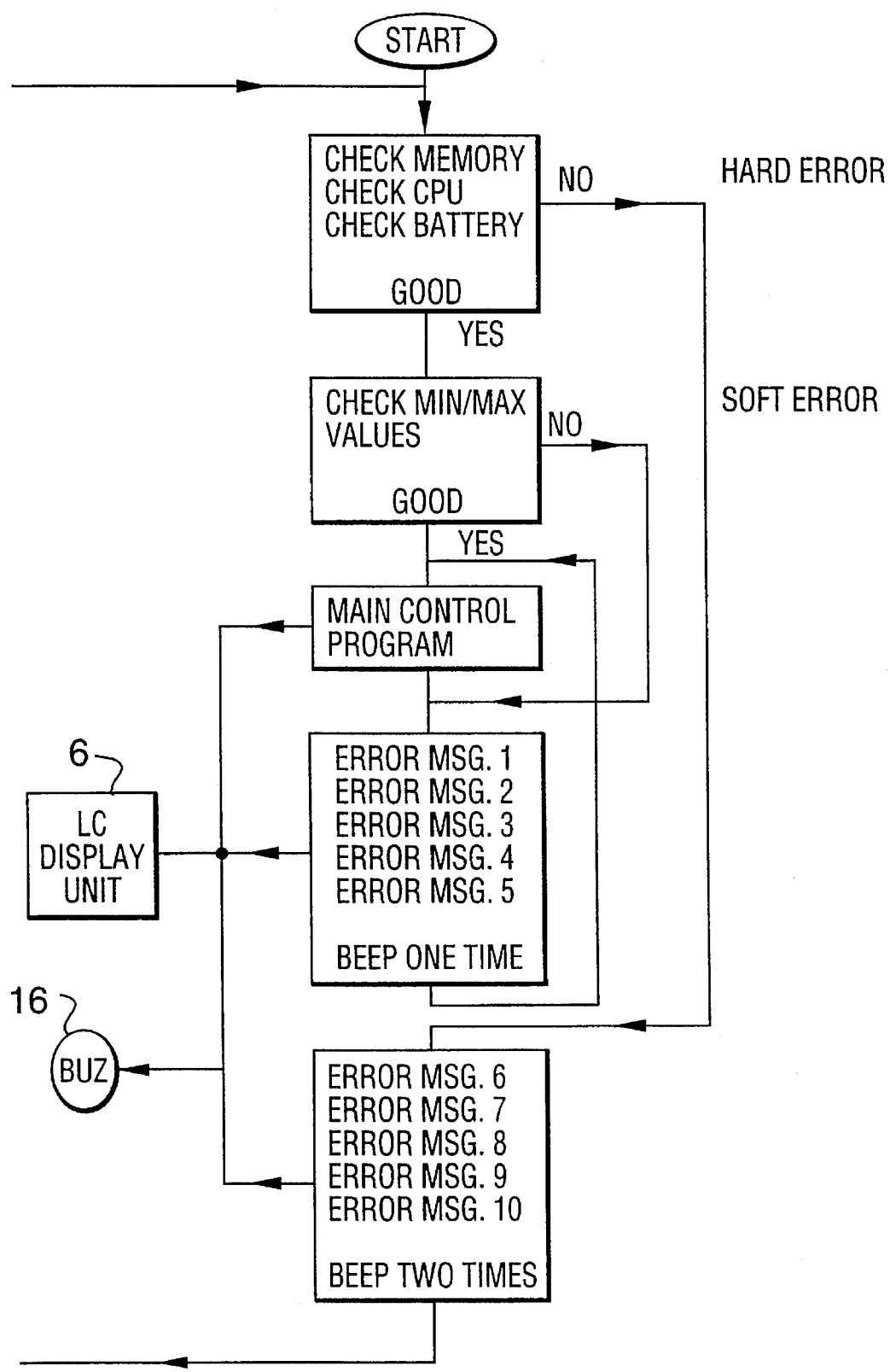
FIG. 6 illustrates a schematic block diagram of the error checking flow chart of the microcontroller.

FIG. 6 illustrates a schematic block diagram of the error checking flow chart of the software program of the microcontroller. Connections to the piezobuzzer 16 and liquid crystal display unit 6 are shown.

The schematic block diagram illustrated in FIGS. 5 and 6 are presented herein for completeness of disclosure. As indicated previously, the microcontroller unit can be purchased from Motorola, Model No. MC68HC705P9. Since the microprocessor unit can be purchased from Motorola, it is not considered necessary to discuss in detail the function and operation of the microprocessor unit.

Figure 7:
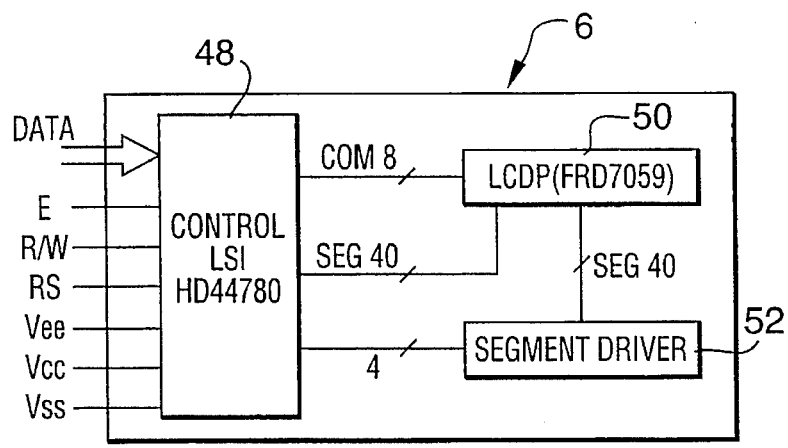
FIG. 7 illustrates a schematic block diagram of the liquid crystal display panel of the demand oxygen controller and respiratory monitor.

FIG. 7 illustrates a schematic view of the functional components of the liquid crystal display 6. The LSI control 48 of the display 6 receives data as indicated by the arrow and power from the microcontroller 26 (not shown). The control 48 is electronically connected to the liquid crystal display 50 and segment driver 52 as indicated. This liquid crystal display 6 can be purchased from Motorola, Model No. DMC16106A. The liquid crystal display panel 6 has the following features: (1) The display is of the liquid crystal type for low power consumption; (2) The panel requires only low voltage which makes it suitable for battery use; (3) The panel is compact and of lightweight design which can be easily assembled in a device; (4) The panel has graphic, figure, and character displays; (5) The panel interfaces with 8-bit or 4-bit micro; (6) The panel displays 192 kinds of alphabets, numerals, symbols and special characters; (7) The panel requires only a single power supply of +5 volts. Other suitable displays are available in the marketplace. The liquid crystal display panel 6, available from Motorola under Model No. DMC16106A, has a typical input "high" voltage of 2.2 volts, a typical input low voltage of 0.6, an output high voltage of 2.4 and an output low voltage of 0.4. The supply current is typically 2 to 4 mA. The supply voltage for logic ($V_{cc}-V_{ss}$) is typically −0.3 to 7 volts, supply voltage for the LCD drive $V_{cc}-V_{ee}$ is typically 13.5 to 0.3, input voltage is typically −0.3 to 0.3 and operating temperatures are from 0° to 50° C.

The liquid crystal display panel 6 can display any one of the following: low battery alarm; apnea alarm; battery charge; oxygen flow; oxygen flow rate; time/date; average pulse rate of the patient; average pulse off-time of the patient; an alert to reset the computer; and an error number. Other data can be sensed and programmed into the microcontroller 26 as required.

Figure 8:
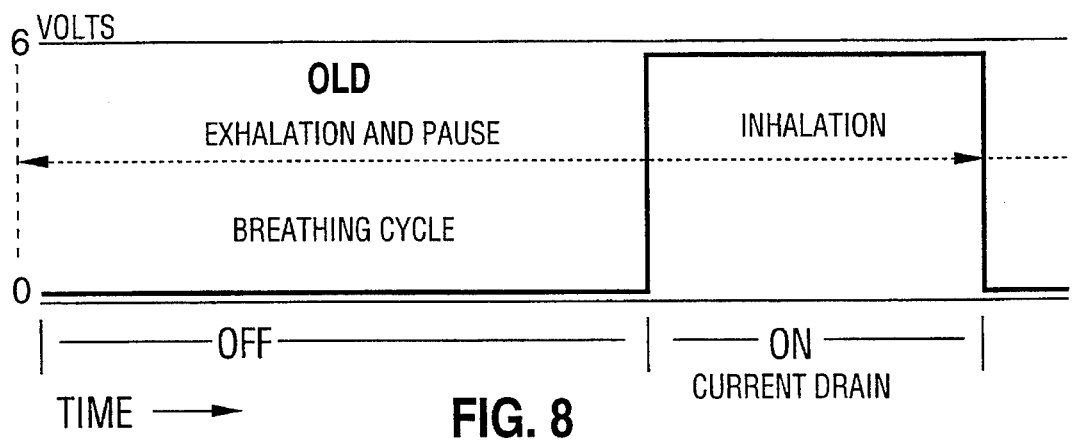
FIG. 8 illustrates a voltage over time graphical depiction of current consumed by a flow control valve of a conventional demand oxygen controller and respiratory monitor.

FIG. 8 illustrates a voltage over time graphical depiction of the electrical current drain of a conventional demand oxygen supply unit. The electrical current from the power supply is on during the entire user inspiration part (shown at the right) of the respiratory cycle. This means that current is drained during the entire inspiration part of the respiration cycle. This results in excessive current requirements and defeats the possibility of a conventional monitor being able to run for any length of time on a battery.

Figure 9:
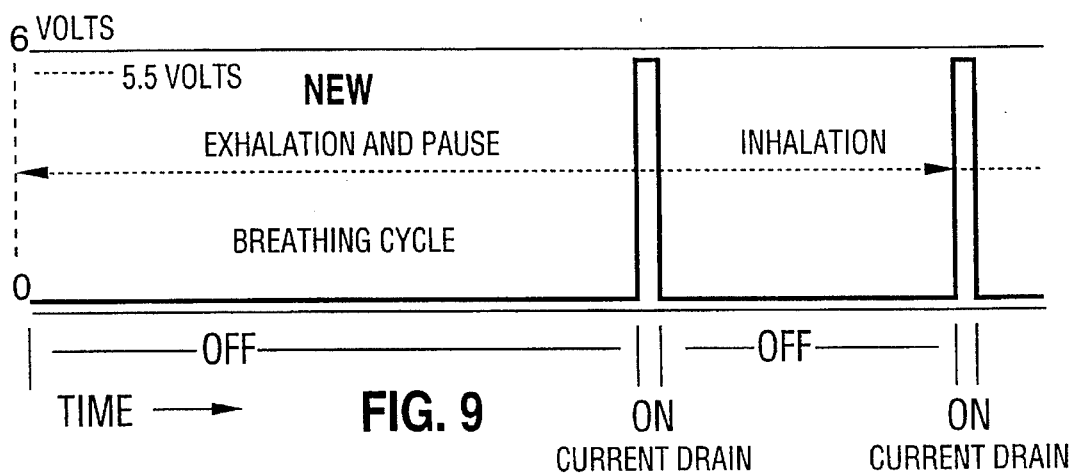
FIG. 9 illustrates a voltage over time graphical depiction of current consumed by a flow control valve of the demand oxygen controller and respiratory monitor.

FIG. 9 illustrates a voltage over time graphical depiction of the electrical current drain of the demand oxygen supply unit. As can be seen, there is a brief flow of current at the beginning of inspiration in order to activate the step control relay 39 to an "on" position, where it remains, and commence flow of oxygen or oxygen-air to the user coincident with the beginning of the inspiration part of the user respiratory cycle. Once activated, the step control relay 39 does not require any further current to remain in the "on" position. Then, at the end of the inspiration phase of the user, there is a second brief flow of current to deactivate the step control relay 39, ie. move it to an "off" position, and thereby stop the flow of oxygen or oxygen-air to the user. The brief periods of electrical current requirement for activating and deactivating the relay 39 mean that a battery power supply, such as the rechargeable lithium battery 24 shown in FIG. 4, can be used to power the system. This enables the controller and respiratory monitor 2 to be used for extended periods of time in a portable environment. The system will operate for a whole day on one battery charge.

Figure 10:
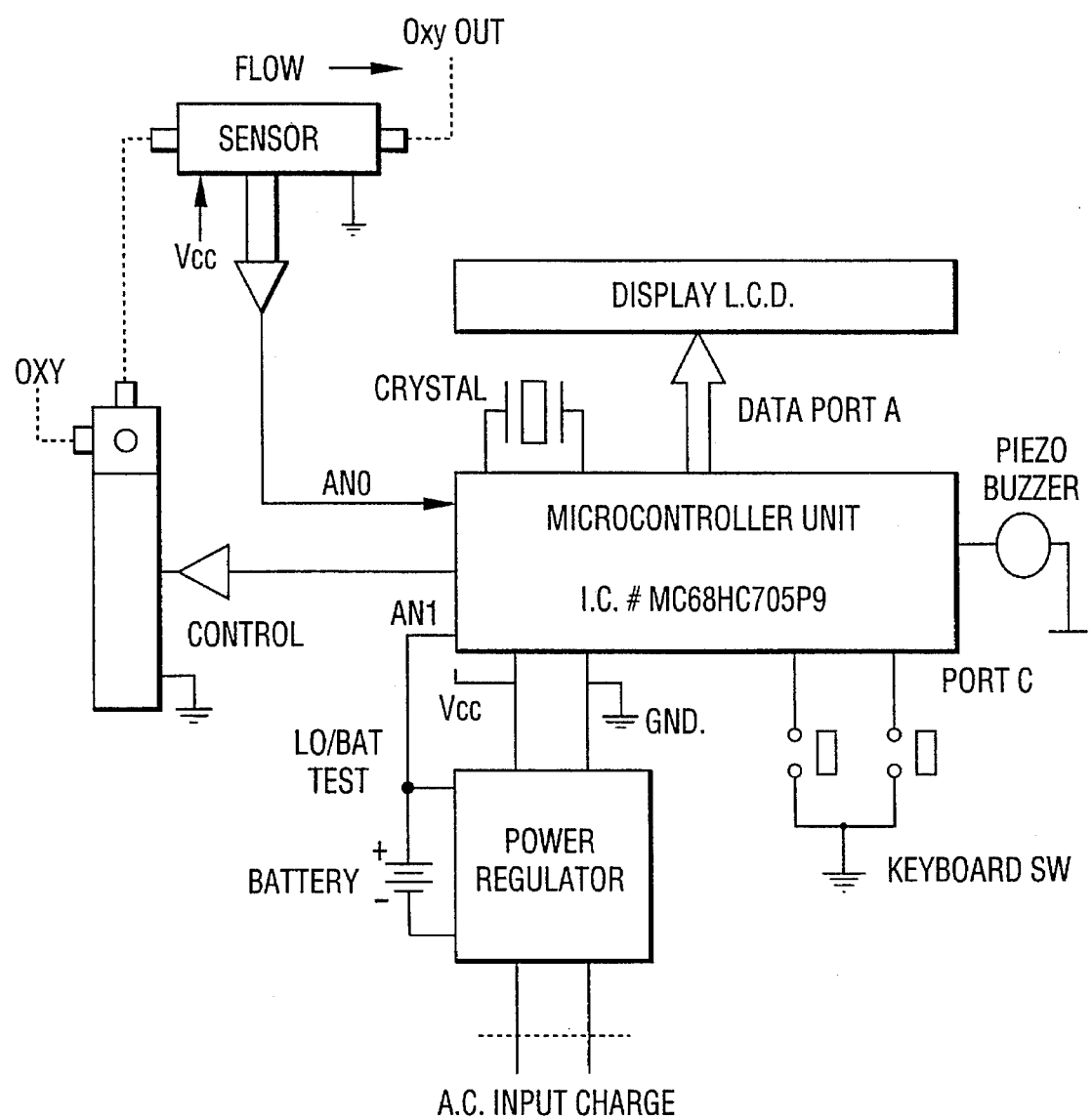
FIG. 10 illustrates a schematic diagram of the electronic components of an alternative embodiment of the demand oxygen controller and respiratory monitor.

FIG. 10 illustrates an alternative embodiment of the demand oxygen controller and respiratory monitor 2 without the keyboard switch 15 with buttons 17, 19 and 21, and data output unit 14 (as shown in FIG. 2). This embodiment is intended as a less expensive unit for applications where the user does not wish to have the facility to adjust the monitor 2, nor connect the monitor to a computer and printer. This embodiment runs on automatic mode. Otherwise, the embodiment is similar to that discussed previously in association with FIGS. 1 through 9 inclusive.

Figure 11:
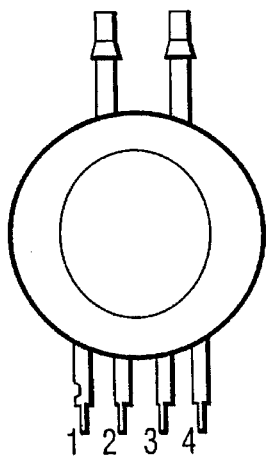
FIG. 11 illustrates a plan view of the sensor with identified pin numbers.
Figure 12:
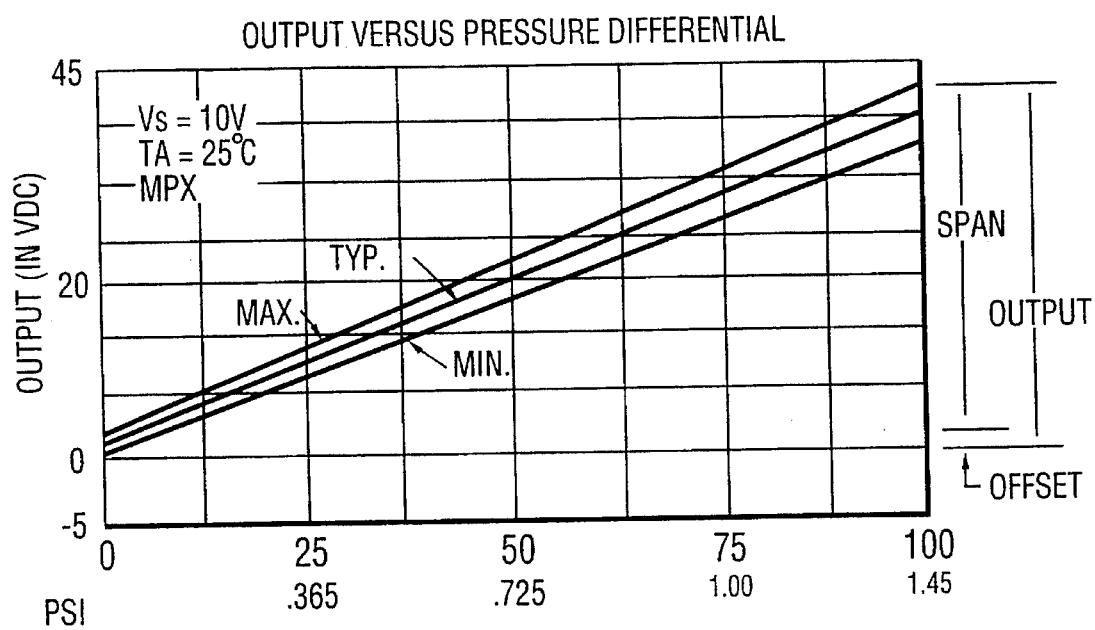
FIG. 12 illustrates a graphical depiction of output voltage vs. pressure differential of the sensor.
Figure 13:
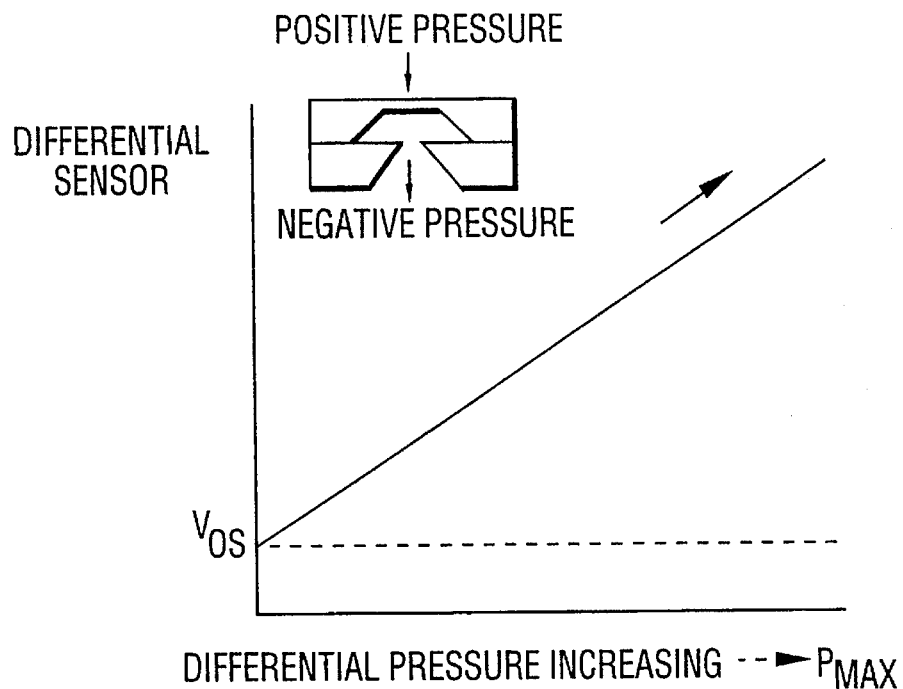
FIG. 13 illustrates a graphical depiction of voltage vs. differential pressure for a differential sensor.
Figure 14:
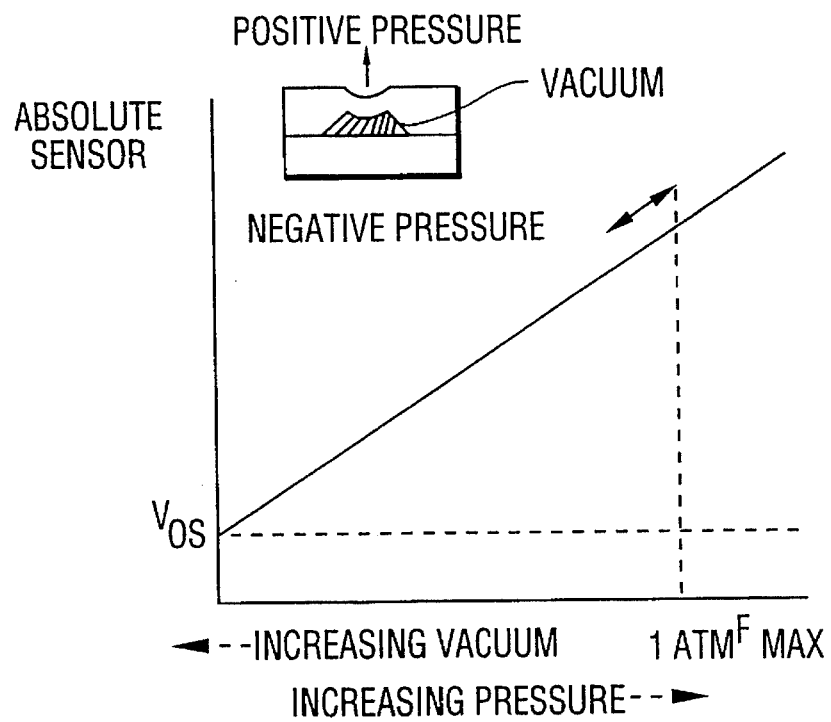
FIG. 14 illustrates a graphical depiction of voltage vs. pressure for an absolute sensor.
Figure 15:
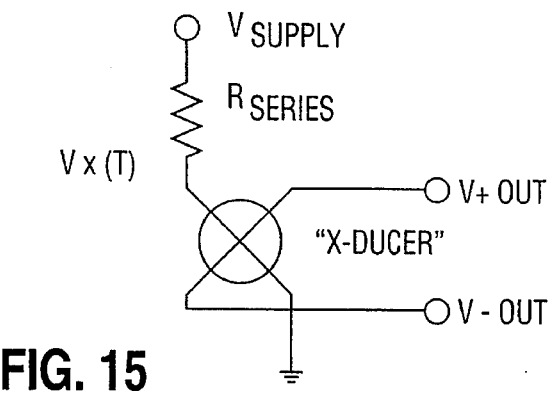
FIG. 15 illustrates a schematic circuit diagram for a sensor with series compensation with constant voltage excitation.
Figure 16:
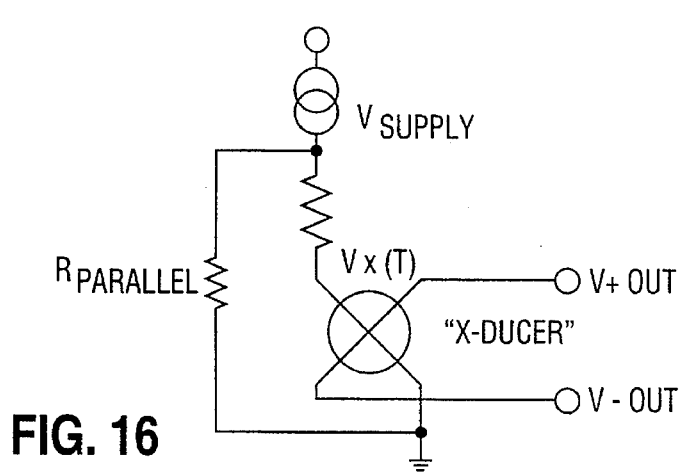
FIG. 16 illustrates a schematic circuit diagram for a sensor utilizing parallel compensation with constant current excitation.

FIG. 11 illustrates a plan view of the sensor with identified pin numbers. FIG. 12 illustrates a graphical depiction of output voltage vs. pressure differential of the sensor. FIG. 13 illustrates a graphical depiction of voltage vs. differential pressure for a differential sensor. FIG. 14 illustrates a graphical depiction of voltage vs. pressure for an absolute sensor. FIG. 15 illustrates a schematic circuit diagram for a sensor with series compensation with constant voltage excitation. FIG. 16 illustrates a schematic circuit diagram for a sensor utilizing parallel compensation with constant current excitation.

The MPX pressure sensitive transducer is ideal for highly sensitive pressure sensing needs. It has excellent long term repeatability at ±0.5% PS (typ) after 1.5 million pressure cycles and 1000 temp. cycles. The leads are positioned on standard PC board spacing. The output is an analog signal proportional to pressure input and ratio-metric to supply voltage. Gauge and differential devices may be used above atmospheric pressure as well as in vacuum applications. All silicon pressure transducers are piezoresistive devices which produce a charge in output voltage when a sensing element's resistance changes. The sensing element is used as one of four resistors in a wheatstone bridge, acting as an electromechanical analog of a hall effect device.

Figure 17:
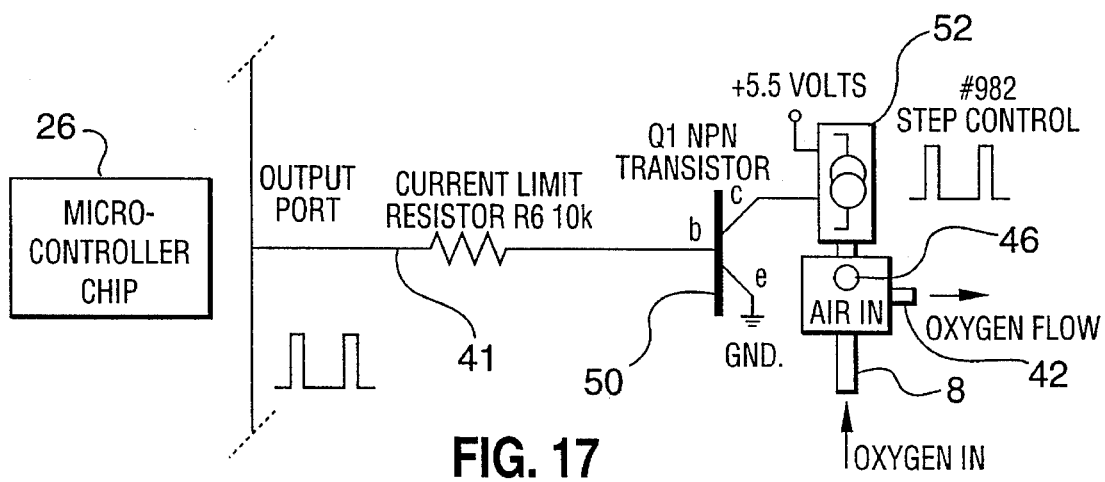
FIG. 17 illustrates a schematic electromechanical diagram of the step control relay incorporating a step controlled latching solenoid.

FIG. 17 illustrates a schematic electromechanical diagram of the step control relay 39 incorporating a step controlled latching solenoid. An output pulse from the microcontroller 26 is sent via line 41 to the base of Q1 transistor 50. Transistor 50 controls solenoid 52 which is of the latching type. The solenoid 52 is opened by a brief pulse of electrical current and stays open without drawing further current. Then, when it is desired to turn off the solenoid 52, when inspiration terminates, the microcontroller sends another brief output pulse to the solenoid 52 to turn it off. The on-off solenoid 52 controls the inflow of oxygen through port 8, and optionally air through inlet 56 and the outflow of oxygen or air and oxygen, as the case may be, through outlet 42, according to the two brief pulse step control electrical current pattern shown in FIG. 9.

OPERATION

The monitor 2 illustrated in FIG. 1 is connected by line 8 to a supply of respirating gas, typically oxygen. Gas (oxygen) delivered through input line 8 is maintained at a relatively constant pressure, typically about 20 psig, by means of a pressure regulator (not shown). Optionally, air can be introduced through input 46 (see FIG. 4) and blended with the oxygen. The oxygen or the blended mixture is delivered to sensor 38 via line 42. The outlet port 10 of sensor 38 is connected to a cannula or other delivery system which terminates in nares or a mask (not shown) worn by the user. In many cases, sufficient air mixes with the oxygen at the point of exit from the cannula or mesh that it is not necessary to use air input through input 46.

In use, oxygen from source through input 8 at a pressure controlled by the regulator flows directly to step control relay 39. In one embodiment of the relay 39, it effects a preset displacement equal to a unit dose, for one breath, of oxygen measured at standard ambient conditions in accordance with the user's inspiration demands as determined by the sensor 38 and regulated by the microcontroller 26. Step control relay 39 performs two distinct functions. First, it premeters or measures a quantity or mass of gas (oxygen or oxygen and air) equal to the prescribed unit dose for one inhalation breath of the user. Second, it temporarily parks or stores that premetered quantity, or unit dose and then releases that stored unit dose in synchronization with the onset or start of the user's inhalation. By first premetering and then temporarily storing each single or unit dose of gas, the source of respirating gas is always isolated from direct communication with the user by the step control relay 39 thereby providing a significant safety feature.

It is conventional to express a unit dose of respirating gas in terms of a gas volume at standard temperature and pressure. Gas dispensing means of this general type typically operate at ordinary room temperature so gas volume changes due to temperature variations may be safely ignored. Hence, the operating volume of both types is dependent upon the pressure of the gas source. For example, if the volume of oxygen prescribed for one breath or unit dose is 33 cc (approximately equal to a continuous rate of 2 liters per minute), then the required displacement volume of the first step control relay 39 at a source pressure of 20 psig would be about 14 cc.

Each dose of oxygen must be delivered in synchronization with the user's inspiratory cycle. To accomplish efficient synchronous delivery, the invention utilizes an extremely sensitive and fast responding sensor 38 which is operably connected to cannula by means of line 10. The sensor 38 is much more sensitive than a thermocouple type sensor, and consumes much less electrical current. A suitable sensor 38 which monitors and responds to slight changes of pressure occurring in the nasal cavity of the user has been described above.

Sensor 38 is arranged to produce an electrical signal upon detection of the beginning of an inhalation by the user. The signal is transmitted via control 45 and connection 40 to microcontroller 26. Microcontroller 26, responding to the electrical signal from sensor 38, activates via connection 41 and control 43, and battery connection line 33, a brief electrical current surge (see FIG. 9) which triggers a solenoid valve (not shown but see FIG. 17) in relay 39 to move to its open position, to permit oxygen to enter the relay 39. This oxygen source is isolated from the remainder of the system and the unit dose of oxygen in relay 39 (mixed with air if desired) surges through line 42, then through sensor 38 and finally through outlet 10 into the cannula and thence to the user, who then inhales it. At the end of the inspiration phase, the sensor 38 senses this termination and sends another brief electrical signal to the microcontroller 26. A brief electrical signal is then sent by the microcontroller 26 to relay 39 upon completion of the delivery of a unit dose of oxygen to the user, thereby initiating another brief surge of current from the battery 24, and resetting the valve in relay 39 to its original off position, thus beginning the cycle anew.

The cycle of two brief electrical current pulses travelling through connectors 28, 30, 33, 40 and 41 to activate or deactivate the solenoid valve in the relay 39 thereby causing it to move to its respective reciprocal on or off position, wherein inlet port 8 is alternatively connected to outlet port 10 and disconnected from outlet port 10, should be brief but, at the same time, of long enough duration to permit the valve to return to its original or reset position and await the next trigger signal. The exact duration of the electric power pulse produced by the microcontroller 26 should also be sufficiently long to permit complete delivery of the stored oxygen volume in the displacer chamber of the relay 39 but short enough to allow sufficient time for the metering chamber to refill with oxygen or air and oxygen in certain embodiments in time for the next cycle. A range of electrical current flow times from about ⅜ to ¾ of a second is generally appropriate with a period of ½ second being a good design target.

In a more complex embodiment of this invention, the cannula or other gas delivery means to the patient is never in direct communication with the source of the respirating gas. Prior art devices can be generally characterized as providing direct communication or an open flow path between the source of the respirating gas and the patient while gas delivery is in progress. A simple embodiment of the invention, however, can also have a direct flow path. Pre-metering and temporarily storing each unit dose of respirating gas in the more complex embodiment inherently provide safety features not present in most conventional gas delivery systems.

By a combination of sensing with the sensor 38 the time length of the respiration cycle of the user, the volume of respiration gas delivered during each inspiration phase, and over a given time, and sensing pulse via the oximeter sensor input 36, when present in a more complex embodiment, tabulated over time, the microcontroller 26 can track and store this data. The appropriate data can be called up for display on the liquid crystal display 6 by activating buttons 17, 19 or 21. The microcontroller 26 can also be programmed to track battery charge, level, termination of breathing cycle, or power outage, or malfunction. This data can also be called up on the display 6, or used in optional embodiments to activate LED lights or the piezobuzzer 16, or send a message via data port 14 to a separate computer, alarm or pager operated by a nurse, attendant or physician.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A portable apparatus for carrying by a person and supplying dosages of an oxygen-containing gas in synchronization with the inhalation phase of the respiratory cycle of a person, comprising:

(a) a low voltage step control relay having a gas inlet port on the apparatus adapted for connection to a source of oxygen-containing gas; means for reciprocally moving said step control relay from a closed non-gas flow position to an open gas flow position responsive to an electrical signal from a microcontroller of sufficient length of time to open said step control relay, for maintaining said step control relay, after being opened, in an open gas flow position without drawing further electrical current, and for moving said step control relay from an open gas flow position to a closed non-gas flow position responsive to a subsequent electrical signal from a microcontroller of sufficient length of time to close said step control relay;

(b) a low voltage microbridge mass gas flow sensor connected to a gas outlet port on the apparatus, said gas flow sensor sensing the commencement of inhalation, the duration of oxygen containing gas flow, and the termination of inhalation during each inhalation phase of the respiratory cycle and transmitting corresponding commencement, duration and termination information to a microcontroller;

(c) a programmed low voltage microcontroller for receiving a first electrical signal from the gas flow sensor upon detection by the gas flow sensor of the commencement of inhalation, and for transmitting said first electric signal to the step control relay of sufficient duration to cause the step control relay to move to said open gas flow position; and for receiving a second electrical signal from the gas flow sensor upon detection by the gas flow sensor of the termination of inhalation, and for transmitting said second electric signal to the step control relay of sufficient duration to cause the step control relay to move to said closed non-gas flow position;

(d) a portable low voltage electrical power supply for operating the low voltage step control relay, the low voltage gas flow sensor and the low voltage microcontroller;

(e) a display on the apparatus connected to the microcontroller and the gas flow sensor for displaying programmed data from said microcontroller, and data received from said gas flow sensor;

(f) a keyboard on the apparatus connected to said microcontroller for enabling manual control commands to be conveyed to said microcontroller; and (g) said apparatus having a total mass capable of being carried by a single person.

2. An apparatus as claimed in claim 1 wherein the step control relay comprises an on-off reciprocating valve incorporating a step controlled latching solenoid.

3. An apparatus as claimed in claim 2 wherein the gas flow sensor is constructed of dual sensing elements flanking a central heating element, and by means of an unsupported thin film with low heat capacity, senses the commencement and the termination of gas flow inhalation.

4. An apparatus as claimed in claim 1 wherein the step control relay has an oxygen inlet port and an air inlet port, and is equipped with a regulator that blends the oxygen and the air according to a ratio determined by the microcontroller.

5. An apparatus as claimed in claim 1 wherein the microcontroller is electronically supported by a crystal which acts as a time base and time regulates the microcontroller.

6. An apparatus as claimed in claim 1 wherein the display is a low voltage liquid crystal display.

7. An apparatus as claimed in claim 6 including random access memory connected to said microcontroller and said liquid crystal display.

8. An apparatus as claimed in claim 7 including a data output port on the apparatus which is connected to said microcontroller and enables said apparatus to be connected to an exterior microprocessor.

9. An apparatus as claimed in claim 6 wherein the keyboard includes a manual control which enables a person to call up assorted programmed messages or data on the liquid crystal display.

10. An apparatus as claimed in claim 1 wherein said microcontroller is connected to a piezobuzzer on the apparatus, said microcontroller activating said piezobuzzer responsive to a predetermined condition programmed into the microcontroller occurring.

11. An apparatus as claimed in claim 1 including an oximeter sensor means adapted to be connected between a person and the microcontroller for monitoring the pulse rate of a person using the apparatus.

12. An apparatus as claimed in claim 10 wherein said keyboard includes a manual control which enables said microcontroller to operate in a programmed automatic mode.

13. An apparatus as claimed in claim 1 wherein said step control relay, said gas flow sensor, said microcontroller, and said electrical power supply are housed in a protective case, the display panel and keyboard are mounted on the exterior of said case, and the gas inlet port and the gas outlet port are mounted in the exterior walls of the case.

14. An apparatus as claimed in claim 13 wherein a cannula or mask is connected to said gas outlet port gas pressure changes in said cannula or mask being sensed by said gas flow sensor, which responds to gas pressure changes indicative of the commencement or termination of inhalation, and transmits corresponding electrical signals to the microcontroller.

15. An apparatus as claimed in claim 1 wherein the portable power supply is a rechargeable long-life battery.

16. An apparatus as claimed in claim 15 wherein the battery is a rechargeable lithium battery.

17. An apparatus as claimed in claim 15 including a light emitting diode on the apparatus which illuminates when the electrical current level of the battery drops below a predetermined level.

18. An apparatus for carrying by a person and supplying dosages of an oxygen-containing gas to the respiratory tract in synchronization with the inhalation phase of the respiratory cycle comprising:

(a) a low voltage step control relay with an on-off reciprocating valve with a step-controlled latching solenoid, and a gas inlet port on a surface of the apparatus adapted for connection to a source of oxygen-containing gas having a gas proportion regulator; means for reciprocally moving said step control relay from a closed non-gas flow position to an open gas flow position responsive to an electrical signal from a microcontroller of sufficient length of time to open said step control relay, for maintaining said step control relay in an open gas flow position without drawing further electrical current, and for moving said step control relay from a gas flow open position to a closed non-gas flow position responsive to with a subsequent electrical signal from a microcontroller of sufficient length of time to close said step control relay;

(b) a low voltage microbridge mass gas flow sensor constructed of dual sensing elements flanking a central heating element, and said gas flow sensor by means of unsupported thin film with low heat capacity, sensing gas flow, said gas flow sensor being connected to a gas outlet port on a surface of the apparatus and adapted to be connected to the respiratory tract of a person, said gas flow sensor sensing the commencement of inhalation, the duration of oxygen containing gas flow, and the termination of inhalation, during each inhalation phase of the respiratory cycle and transmitting corresponding commencement, duration and termination information to a microcontroller;

(c) a programmed low voltage microcontroller for receiving a first electrical signal from the gas flow sensor upon detection by the gas flow sensor of the commencement of inhalation, and for transmitting said first electric signal to the step control relay of sufficient duration to cause the step control relay to move to said open gas flow position; and for receiving a second electrical signal from the gas flow sensor upon detection by the gas flow sensor of the termination of inhalation, and for transmitting said second electric signal to the step control relay of sufficient duration to cause the step control relay to move to said closed non-gas flow position;

(d) a portable low voltage rechargeable lithium battery for supplying electrical power for operating the low voltage gas flow sensor, the low voltage step control relay, and the low voltage microcontroller;

(e) a liquid crystal display panel on the surface of the apparatus connected to the microcontroller and the gas flow sensor for displaying programmed data from said microcontroller, and data received from said gas flow sensor;

(f) a keyboard on the surface of the apparatus connected to said microcontroller for enabling manual commands to be conveyed to said microcontroller; and (g) a cannula or mask connected to said gas outlet port, gas pressure changes in said mask or cannula being sensed by said gas flow sensor, which responds to gas pressure changes indicative of the commencement or termination of inhalation, and transmits corresponding electrical signals to the microcontroller; and (h) said apparatus having a total mass capable of being carried by a single person.

19. An apparatus as claimed in claim 1 wherein the microcontroller tallies the cumulative sum of oxygen consumed over a given length of time.

* * * * *